United States Patent [19]

Boyd

[11] Patent Number: 4,977,585
[45] Date of Patent: Dec. 11, 1990

[54] SELF SHIELDED COMPUTERIZED TOMOGRAPHIC SCANNER

[75] Inventor: Douglas P. Boyd, San Mateo County, Calif.

[73] Assignee: Imatron, Inc., South San Francisco, Calif.

[21] Appl. No.: 334,076

[22] Filed: Apr. 5, 1989

[51] Int. Cl.⁵ .............................................. G01N 23/00
[52] U.S. Cl. ............................................ 378/4; 378/19
[58] Field of Search ...................................... 378/4–20, 378/57, 203, 204, 210

[56] References Cited

U.S. PATENT DOCUMENTS

| | | | |
|---|---|---|---|
| 3,432,657 | 3/1969 | Slavin | 378/15 |
| 3,980,889 | 9/1976 | Haas et al. | 378/57 |
| 4,090,079 | 5/1978 | Grassmann | 378/18 |
| 4,099,059 | 7/1978 | Distler | 378/17 |
| 4,131,802 | 12/1978 | Braden et al. | 378/20 |
| 4,239,969 | 12/1980 | Haas et al. | 378/57 |

Primary Examiner—Craig E. Church
Attorney, Agent, or Firm—Flehr, Hohbach, Test Albritton & Herbert

[57] ABSTRACT

A compact computerized tomographic x-ray scanner having a patient tunnel in which the walls and the ends of the patient tunnel include shielding material to form a shielded enclosure in which the patient body portion is scanned.

3 Claims, 3 Drawing Sheets

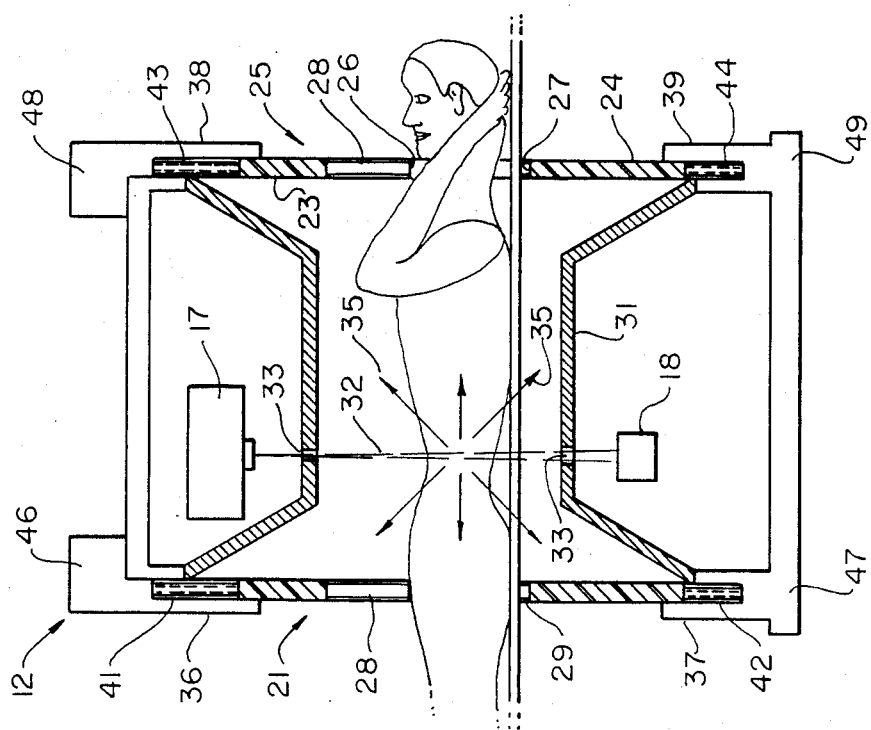
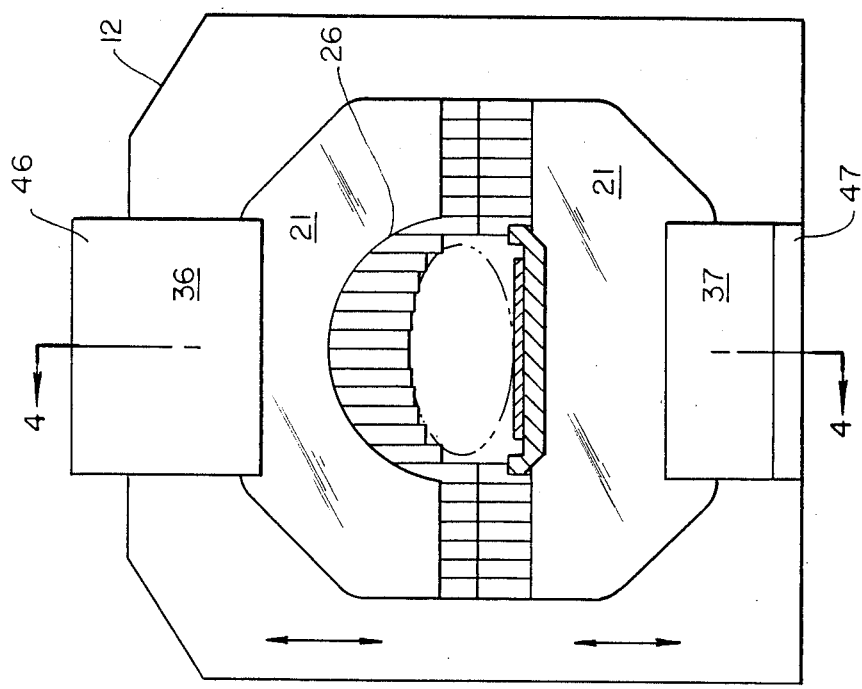
FIG. 4
FIG. 3

SELF SHIELDED COMPUTERIZED TOMOGRAPHIC SCANNER

BRIEF DESCRIPTION OF THE INVENTION

This invention relates generally to a compact computerized tomographic (CT) x-ray scanner and more particularly to a self-shielded computerized tomographic scanner.

BACKGROUND OF THE INVENTION

The use of CT for imaging structures within the head and body has revolutionized the diagnosis and care of patients. The high-resolution images obtainable with currently available CT scanners combined with advanced computer image processing methods provide the capability for truly three-dimensional radiography. One of the most important roles played by CT is its use in the emergency room of large city hospitals. In the traumatized patient, CT examination of the head and body can be performed in minutes, providing the emergency room physician with the immediate information needed for proper management of the patient. Unlike any other imaging modality, CT scans provide in a single image all critical aspects of the traumatized patient. Current concepts of medical practice dictate that CT scanners be located in large referral or trauma centers.

Presently, scanners are located in the x-ray department of hospitals and are housed in expensive shielded rooms. There is a need for a scanner that can be used in a hospital without the necessity of an x-ray shielded room whereby the scanner is transportable and can be moved to the patient location.

Regarding another application of CT scanners, experience in recent wars has proved, that the introduction of computerized tomographic technology into military field hospitals will have a measured impact on diagnostic speed and accuracy of diagnoses with subsequent improved care of patient injuries.

Transportable and self-shielded CT equipment has the potential of reducing the amount and degree of surgical intervention required at support hospitals. This reduction in surgical intervention can ultimately reduce the length of processing time in these hospitals and improve throughout, thus reducing further the required number of field hospital beds. Moreover, CT has an extremely high sensitivity to low-contrast foreign bodies such as plastic shrapnel and is likely to become indispensable for detection and localization of such non-metallic fragments. There is a critical need for a self-shielded mobile or transportable scanner.

SUMMARY AND OBJECTS OF THE INVENTION

It is an object of this invention to provide a self-shielded CT x-ray scanner.

It is a further object of the invention to provide a self-shielded portable or movable CT x-ray scanner.

It is another object of the invention to provide a movable self-shielded CT x-ray scanner system that can be ready for operation within minutes of reaching its destination.

In accordance with the invention, there is provided a self-shielded compact computerized tomographic x-ray scanner of the type including a gantry having spaced faces and a patient tunnel extending between the faces of the gantry with an x-ray source in said gantry to project a fan beam of x-rays across the tunnel through the body of a patient, a detector array for receiving the x-rays and providing an output signal representative of transmission through the patient and a signal processing system for receiving the output signals from the detector array and providing an image of the section of the patient placed in the tunnel.

More particularly, there is provided an x-ray scanner in which the tunnel is lined with a layer of x-ray shielding material and an x-ray shielding curtain is disposed at each of said faces of the gantry to form with said tunnel an enclosed space which shields the surrounds from projected x-rays scattered by the patient and couch.

The foregoing and other objects of the invention will be more clearly understood from the following description taken in connection with the accompanying drawings.

BRIEF DESCRIPTION OF THE DRAWINGS

FIG. 3 is a front elevational view of the CT scanner gantry taken along the lines 3—3 of FIG. 2.

FIG. 4 is a sectional view of the CT scanner of the gantry taken generally along the lies 4—4 of FIG. 2.

DETAILED DESCRIPTION OF THE INVENTION

Figure 1:
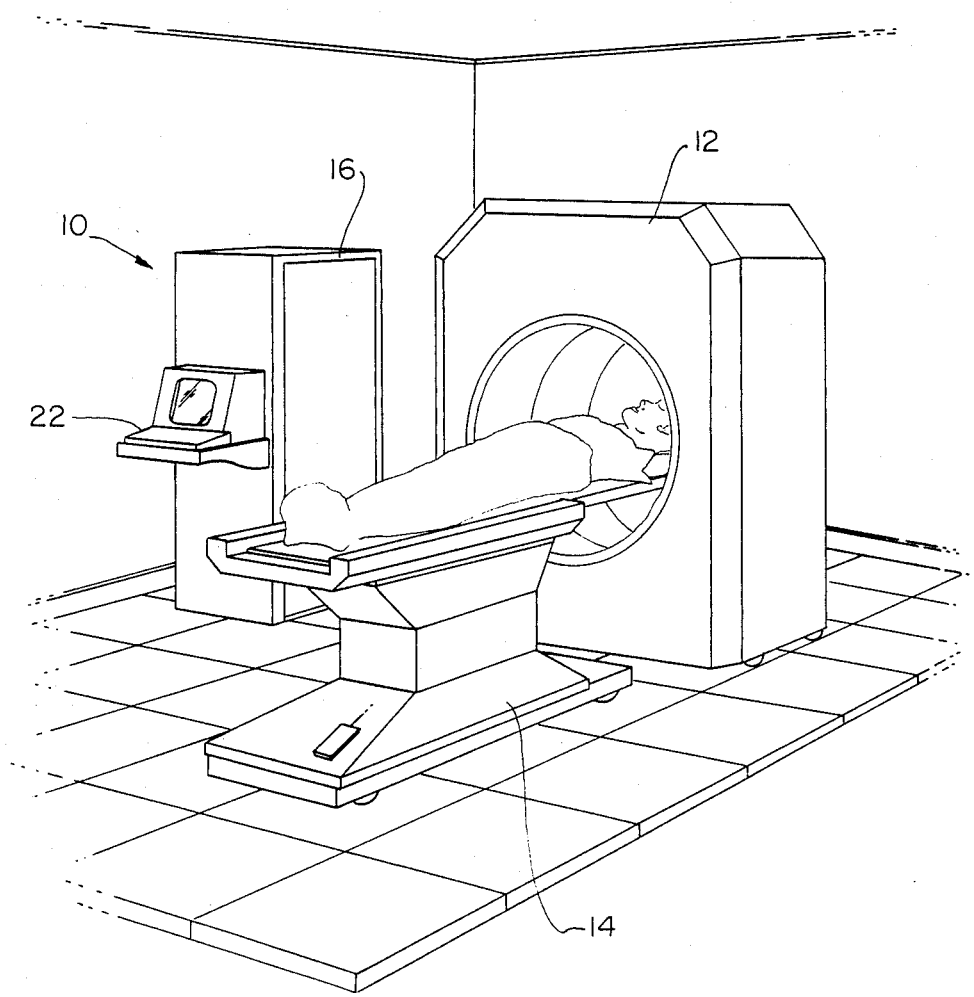
FIG. 1 is a schematic perspective view of a compact CT x-ray scanner in accordance with the prior art.
Figure 2:
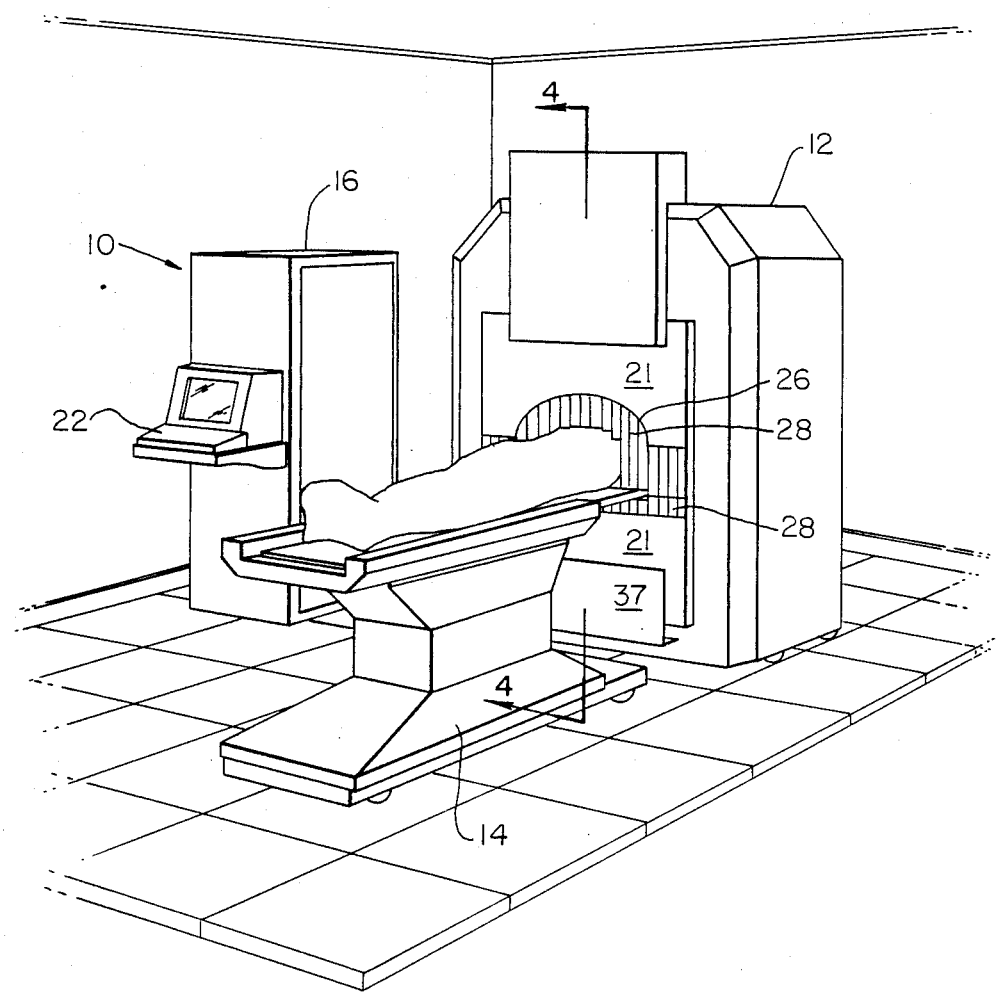
FIG. 2 is a schematic perspective view of a CT x-ray scanner system embodying the present invention.

Referring to the FIGS. 1 and 2 there is shown a compact CT x-ray scanner system 10 according to this invention designed to be transportable. The scanner system 10 includes within this space a scanning gantry 12, a patient couch 14 and a control system 16. Electric power may be provided by a standard portable generator for a field system and from the hospital power for a hospital system. The gantry 12 is of a rotatable type in which the x-ray source, detector and associated electrical circuits are supported by a single support arrangement. The system has an aperture or tunnel large enough to permit rotational scanning of full-body sections.

A special lightweight x-ray tube 17, FIG. 4, and an array of solid-state x-ray detector array 18 of a so-called "rotate-rotate" CT scanner are rotatably supported in the gantry 12. A power supply to power the electronics is included in the control system 16, which is provided with a control keyboard 22.

In accordance with this invention, the CT x-ray scanner system is self-shielding. Referring now particularly to FIGS. 2–4 the gantry 12 is provided with front and rear movable shield curtains 21 and 25. In one embodiment the shields comprise upper and lower clear leaded plastic windows 23 and 24. Such plastic is available from Nuclear Associates, etc. The lower edge 26 of the upper clear window 23 is shaped to conform generally to the body of a patient. The upper edge 27 of the lower window is shaped to conform to the shape of the patient couch 14. Attached to the lower edge 26 of the upper window is a curtain of flexible or pliant material 28 which will conform to the body of a patient when the window is closed. The flexible curtain material may comprise a beaded lead or brass curtain such as described in U.S. Pat. No. 3,967,129. The curtain could also be in multiple strips and layers of lead or strips of flexible leaded plastic. The upper edge 27 of the lower curtain is provided with a flexible curtain material 29 such as lead or leaded plastic strips which can be in multiple layers to provide the necessary shielding. Thus, when the upper and lower windows 23, 24 are moved towards one another they form an effective radiation shield with the patient and couch and with the radiation shield lining 31 which lines the gantry tunnel. The curtains and lining need to have shielding capability equivalent to about 1/32 to 3/32 inches of lead.

FIG. 4 shows the x-ray radiation 32 from the tube 17 passing through the opening 33 in the lead tunnel and penetrating the body of the patient. The transmitted radiation passes through a slot 33 in the lining 31. The transmitted x-rays are detected by the detector array 18. The detector output is stored and processed to form an image of the patient.

Radiation 35 scattered by the patient and other components within the tunnel are absorbed by the movable radiation curtains 23, 24, 28, 29, and the tunnel 31.

Guides and drive means are provided to guide the windows or curtains between the open and closed condition. The windows are guided by brackets 36, 37, 38, 39. Drive means, for example, lead screws 41, 42, 43, 44, engage the windows and are driven by motors housed in housings 46, 47, 48, 49.

In using the scanner, the patient is placed on the patient couch and then positioned inside the gantry tunnel. The radiation shielding curtains are closed, whereby the curtains engage the body and couch to form the radiation containing enclosure. One or more scans with couch incrementations are then performed. If the patient needs to be repositioned, the curtains are opened to allow movement of the patient and then closed for another scan series.

It is seen that stray radiation is shielded by the movable shields and tunnel. This eliminates the necessity for expensive shielded rooms and makes it possible to construct a portable or a transportable scanner for use by the military in the field, and in hospitals.

The present invention has been described above in terms of only one example. However, the example is to be considered as illustrative rather than as limiting. This invention, accordingly, is to be broadly construed and is defined only by the following claims.

What is claimed:

1. In a compact computerized tomographic x-ray scanner of the type including a gantry having spaced faces and a patient tunnel extending between said faces, an x-ray tube in said gantry to project an x-ray beam across said tunnel, a detector array in said gantry for receiving x-rays and providing output signals representative of transmission, a patient couch for introducing a patient into said tunnel, and a signal processing system for receiving the output signal form said detector array providing an image of a section of a patient body placed in the tunnel, the improvement comprising:
   a layer of x-ray shielding material forming a lining for said tunnel; and
   a layer of x-ray shielding material disposed at each of said faces to define with said tunnel a shielded enclosure which shields the surrounds form x-ray scattered by a patient and couch within the enclosure, each curtain comprising two parts movable towards and away from one another whereby the parts are moved away from one another to allow the patent to be introduced into the tunnel and moved towards one another to engage the couch and patient to define the enclosure.

2. A self-shielded computerized tomographic scanner as in claim 1 in which said curtain parts include a rigid portion and a flexible portion which conforms to the shape of the patient and couch.

3. A self-shielded computerized tomographic scanner as in claim 1 including means for guiding said curtains for movement towards and away from one another.

* * * * *